United States Patent [19]

Discher

[11] Patent Number: 5,668,342

[45] Date of Patent: Sep. 16, 1997

[54] APPARATUS AND METHOD FOR DETECTION AND NEUTRALIZATION OF CONCEALED EXPLOSIVES

[76] Inventor: Stephen R. W. Discher, 202 Jones St., Navasota, Tex. 77868

[21] Appl. No.: 568,581

[22] Filed: Dec. 7, 1995

[51] Int. Cl.[6] .................................................. F42B 33/00
[52] U.S. Cl. ........................... 86/50; 86/1.1; 102/293; 588/202
[58] Field of Search ..................... 86/50, 1.1; 102/293; 888/202

[56] References Cited

U.S. PATENT DOCUMENTS

| | | | |
|---|---|---|---|
| 2,917,927 | 12/1959 | Clark | 86/50 |
| 3,075,461 | 1/1963 | Ehlmann | 86/50 |
| 3,568,411 | 3/1971 | Dravnicks et al. | 55/208 |
| 3,601,054 | 8/1971 | Christianson | 102/66 |
| 3,793,101 | 2/1974 | Mullarkey | 86/50 |
| 3,820,479 | 6/1974 | Fylling | 86/50 |
| 4,055,249 | 10/1977 | Benedick et al. | 206/3 |
| 4,202,200 | 5/1980 | Ellson | 73/3 |
| 4,251,726 | 2/1981 | Alvarez | 250/302 |
| 4,621,559 | 11/1986 | Ohlson | 86/50 |
| 4,848,233 | 7/1989 | Dow et al. | 102/202.2 |
| 4,941,162 | 7/1990 | Vartsky et al. | 378/3 |
| 4,980,901 | 12/1990 | Miller | 378/45 |
| 5,006,299 | 4/1991 | Gozani et al. | 376/159 |
| 5,078,952 | 1/1992 | Gozani et al. | 376/159 |
| 5,124,709 | 6/1992 | Baron et al. | 342/192 |
| 5,267,665 | 12/1993 | Sanai et al. | 220/88.1 |
| 5,274,356 | 12/1993 | Taricco | 340/515 |
| 5,356,958 | 10/1994 | Matthews | 523/219 |
| 5,367,552 | 11/1994 | Peachmann | 378/57 |
| 5,401,944 | 3/1995 | Bravman et al. | 235/375 |

FOREIGN PATENT DOCUMENTS 4112470  10/1992  Germany ................................... 86/50

*Primary Examiner*—Harold J. Tudor
*Attorney, Agent, or Firm*—Sidley & Austin

[57] ABSTRACT

A device for detecting and neutralizing an explosive device concealed in cargo by directing a plurality of energies or fields including electromagnetic, electrostatic, magnetic, or acoustic toward the cargo thereby externally inducing detonation. A blast containment enclosure is used to protect surroundings by containment and redirection of a resulting explosion. A method for the detection and neutralization of explosive devices is also provided.

17 Claims, 2 Drawing Sheets

APPARATUS AND METHOD FOR DETECTION AND NEUTRALIZATION OF CONCEALED EXPLOSIVES

TECHNICAL FIELD OF THE INVENTION

The present invention relates to an apparatus and method for detecting the presence of explosive substances or explosive devices concealed in luggage or cargo. More specifically, the present invention relates to an apparatus or method capable of detecting the presence of an explosive substance or an explosive device and neutralizing the detected substance or device through detonation.

BACKGROUND OF THE INVENTION

Over two million pieces of baggage are checked or carried onto civilian aircraft in the United States every day. This exposes the American traveler to a significant risk from concealed explosive devices. Although most carry-on baggage is scanned by x-ray scanners and trained personnel, scanners to detect explosives or explosive devices in checked baggage or cargo are limited by availability and ability. This invention relates to a device which checks individual pieces or batches of luggage, baggage, freight, goods, merchandise, cargo, and the like (hereafter referred to as "cargo") to detect the presence of concealed explosives, explosive devices, improvised bombs, and the like (hereafter referred to as "explosive devices") and simultaneously neutralizes such explosive devices by causing their premature detonation.

1. Detection of Concealed Explosives

Several categories of apparatus for detecting the presence of concealed explosive devices are known. A first category of apparatus, known as "explosives sniffers," operate by collecting a sample of air from the vicinity of the cargo and employing sensors which respond to the vapors emitted by certain types of explosive substances. Such apparatus include: U.S. Pat. No. 4,202,200 to Ellson, "Apparatus for Detecting Explosive Substances"; and U.S. Pat. No. 3,568,411 to Dravnicks et al., "Chemosensor Bomb Detection Device." A limitation of these explosives sniffer apparatus is that they are unable to detect explosive devices utilizing explosive substances which do not emit such characteristic vapors or when plastic, wax, glue, or other sealing agents have been used to contain the tell-tale vapors. A need therefore exists, for an explosive detection apparatus or method which detects concealed explosive devices which do not emit vapors.

A second category of apparatus for detecting concealed explosive devices, known as "nuclear detection" apparatus or "nuclear resonance detectors," operate by irradiating the cargo with beams of neutrons or other radiation which interact with specific elements such as nitrogen, chlorine, and hydrogen within the cargo and causes the release of characteristic secondary radiation which the apparatus then detects and analyzes to determine the presence explosive compounds. Such apparatus include: U.S. Pat. No. 5,078,952 to Gozani et al., "Multi-Sensor Explosive Detection System"; U.S. Pat. No. 5,006,299 to Gozani et al., "Explosive Detection System"; U.S. Pat. No. 4,980,901 to Miller, "Apparatus for and Methods of Detecting Common Explosive Materials"; and U.S. Pat. No. 4,941,162, to Vartsky, et al., "Method and System for Detection of Nitrogenous Explosives by Using Nuclear Resonance Absorption." The disadvantages of nuclear detection apparatus include their inability to detect explosives which do not emit characteristic secondary radiation such as improvised explosive devices of the type often utilized by terrorist entities. A need therefore exists, for an explosive detection apparatus or method which detects concealed improvised explosive devices or explosives which do not emit characteristic secondary radiation.

A third category of apparatus for detecting concealed explosive devices, known as "pressure cycling" apparatus, recognize that terrorist explosive devices may be designed to initiate or detonate only after experiencing multiple pressure "cycles" corresponding to the multiple altitude ascents and descents of an aircraft on different legs of its route. To counter the threat of such pressure sensitive devices, pressure cycling detection apparatus are known which simulate the multiple ascents and descents of an aircraft by repeatedly decreasing and increasing the pressure in a test chamber containing the cargo. An example of such a pressure cycling apparatus is disclosed in U.S. Pat. No. 5,274,356 to Taricco, "Methods and Apparatus for the Inspection of Air Cargo for Bombs." Taricco discloses repeatedly decreasing and increasing the pressure in a test chamber to initiate pressure sensitive explosive devices. Taricco further discloses using electromagnetic noise sensors to detect electromagnetic radiation characteristic of bomb timing devices which may be initiated by the pressure cycles. Disadvantages of the method and apparatus disclosed by Taricco include the limitation to the detection of pressure sensitive explosive devices which emit electromagnetic radiation upon initiation. A need therefore exists, for an explosive detection apparatus or method which detects concealed pressure sensitive explosive devices which do not emit electromagnetic radiation when initiated.

Furthermore, it is desirable for safety reasons in "pressure cycling" detection apparatus to test the cargo with as many pressure cycles as possible to decrease the likelihood that a concealed explosive device may be set for detonation after a greater number of pressure cycles than the number performed in the test. However, it is also desirable, for reasons of economy, to minimize the time required to test each batch of cargo. A need therefore exists, for an explosive detection apparatus or method which simulates a large number of aircraft ascent and decent cycles in a short period of time.

Known explosive detection apparatus of both the explosives sniffer and nuclear detector categories previously discussed function only to detect explosive substances. Such apparatus contain no means for neutralizing an explosive device once one has been detected. U.S. Pat. No. 5,274,356 to Taricco discloses that pressure sensitive explosive devices initiated and detected by pressure cycling apparatus can be allowed to self-detonate within the test chamber. However, since a terrorist explosive device may be equipped with a means for post-initiation delay, such passive neutralization methods may require an unacceptably long time to accomplish the necessary neutralization. A need therefore exists, for an explosive detection apparatus or method which detects concealed explosive devices and expediently neutralizes such explosive devices.

2. Neutralization of Explosive Devices

Most improvised explosive devices of the type used by terrorist entities are initiated by directing electrical current supplied by batteries or other sources through switches, relays, wires and the like to an electro-explosive device such as a blasting cap, squib, commercial detonator, or improvised detonator. These electro-explosive devices include at least one electrical ignition device disposed in ignition relationship with one or more heat sensitive explosive charges and are fired by passing a DC current through a high resistance filament wire or bridge of high electrical resistance which is in heat transferring contact with the first fire mixture. A sufficient flow of current heats the bridge wire to incandescence, thereby igniting the surrounding mixture, thereby detonating other charges. It is well known in the art that such electro-explosive devices are subject to unintended discharge by stray electromagnetic or electrostatic energy. Typically, blasting caps are most vulnerable to unintended detonation when subjected to short bursts of low frequency, high power energy in the radio frequency spectrum. Therefore, by directing bursts of high power, low frequency energy toward an explosive device, detonation of the device may be accomplished. Similarly, electromechanical relays and mechanical switches (including pressure sensitive switches) are vulnerable to unintended actuation when pulsed with strong magnetic fields applied externally to the device. Electromechanical relays, in particular, utilize ferrous metal armatures or reed switches which are typically actuated by solenoids or coils, thereby opening or closing electrical contacts. Therefore, a strong external magnetic field applied nearly parallel to the central axis of the coil or solenoid and opposite to the armature or reed switch will cause actuation of the relay contacts.

Other means of detonating improvised explosive devices include mechanical timers and pressure sensitive switches. By design, mechanical timers employ precision clock movements which are vulnerable to permanent damage when exposed to strong magnetic fields, thereby permanently deforming or dislodging parts of their movement, disabling the explosive device. Pressure sensitive switches, in order to detect slight changes in ambient pressure (which in an aircraft's pressurized cargo hold are less that 10 inches of mercury) must be precision devices in order to be effective. Therefore, any ferrous metal components of the pressure switch such as springs, diaphragms, or contacts are subject to permanent deformation and damage when exposed to strong magnetic fields.

High frequency energy of the type generated by magnetrons or klystrons may, when directed at explosive compounds in short pulses, produce sufficient heat in the material to cause detonation in the same manner as the filament wire of a blasting cap.

Additionally, devices for containing or redirecting explosions, known as detonation chambers, are widely known and used to protect surroundings by containment or redirection of explosions.

3. Additional Factors

While the use of concealed explosive device detectors is most commonly associated with aircraft and airports, increase public safety and confidence will result from the use of such apparatus and methods on all forms of public transportation and places of public accommodation. A need therefore exists, for an explosive detection method or apparatus which is suitable for use with aircraft, trains, ships, boats, busses, public buildings and the like.

Most airports and other enterprises with intensive cargo handling operations utilize automated baggage or cargo handing systems. Such systems are generally very expensive to replace. A need therefore exists, for an explosive detection apparatus or method which can be integrated into known types of airline baggage handling systems.

In some situations, for example the activities of police bomb squads or ordinance disposal teams, it is necessary to detonate and thereby neutralize explosive substances or explosive devices which are known rather than concealed. In some such cases, it is desirable to process large amounts of such substances or devices in a short periods of time with minimal risk to personnel and property. A need therefore exists, for an explosive detection method or apparatus which detonates known explosive substances and explosive devices either singly or in a batch load manner.

SUMMARY OF THE INVENTION

It is an object of the present invention to provide an explosive detection method or apparatus which detects concealed explosive devices which do not emit vapors. It is another object of the present invention to provide an explosive detection method or apparatus which detects concealed improvised explosive devices or explosives which do not emit characteristic secondary radiation. It is still another object of the present invention to provide an explosive detection method or apparatus which detects concealed explosive devices and neutralizes such explosive devices. It is a further object of the present invention to provide an explosive detection method or apparatus which detects concealed pressure sensitive explosive devices which do not emit electromagnetic radiation when initiated. Still another object of the present invention is to provide an explosive detection method or apparatus which simulates a large number of aircraft ascent and decent cycles in a short period of time. It is also an object of the present invention to provide a concealed explosive detection apparatus or method which, in use, will increase passenger safety and confidence on public transportation and public places such as aircraft, trains, busses and public buildings. It is another object of the present invention to provide an explosive detection method or apparatus which can be integrated into known types of airline baggage handling systems and the like. It is a further object of the present invention to provide an explosive detection method or apparatus which detonates known explosive substances and explosive devices either singly or in a batch load manner.

These and additional objects are accomplished by providing an apparatus comprising an isolation enclosure and a detonation inducing system including at least one primary energy source and at least one compatible transducer. The present invention is able to detect and neutralize explosive devices and most known types of explosive substances through premature detonations regardless of the type of initiating device or number of pre-set pressure cycles.

In a first embodiment of the current invention, the cargo to be tested is placed into an isolation enclosure which will contain a possible explosion. When the enclosure is secured, energies and/or fields are directed at the cargo to close detonating relays and switches, directly initiate explosive substances, damage and render inoperable clocks and timers, and/or actuate pressure-sensitive and temperature-sensitive devices, thereby detecting and neutralizing any concealed explosive devices through premature detonation.

All of the functions of the unit may be automated by a programmable logic controller or personal computer to enable the unit to handle a total throughput in excess of 10 pieces per minute.

In a preferred embodiment of the current invention, an apparatus is provided comprising an isolation enclosure including walls and at least one door, a blast absorbent lining positioned inside the enclosure adjacent to the walls and each door, an exhaust duct attached to an opening formed through a wall of the enclosure and including a flapper valve and a shrapnel screen, a plurality of transducers positioned inside the enclosure between the interior of the enclosure wall and the blast absorbent lining, each transducer adapted for directing a selected type of secondary energy or field into the test chamber upon receipt of a selected type of primary energy, primary energy sources for the generation of the selected type of primary energy and operatively connected to compatible transducers so that the selected type of primary energy is delivered to each transducer, a transfer apparatus adapted to move the batch loads of cargo into and out of said test chamber through the doors, a scanning device positioned to allow scanning the batch load prior to moving the batch load into the test chamber, an explosion sensor adapted to detect the occurrence of an explosion within the test chamber and a control unit operatively connected to the transfer apparatus, the scanning device, the doors, the primary energy sources and the explosion sensor.

Additionally, this invention provides a particular method for utilizing multiple energy generators whose energy is transmitted through transducer arrays toward the suspect cargo in a controlled environment. The presence of concealed explosives is detected and neutralized by a successful detonation.

DETAILED DESCRIPTION

Figure 1:
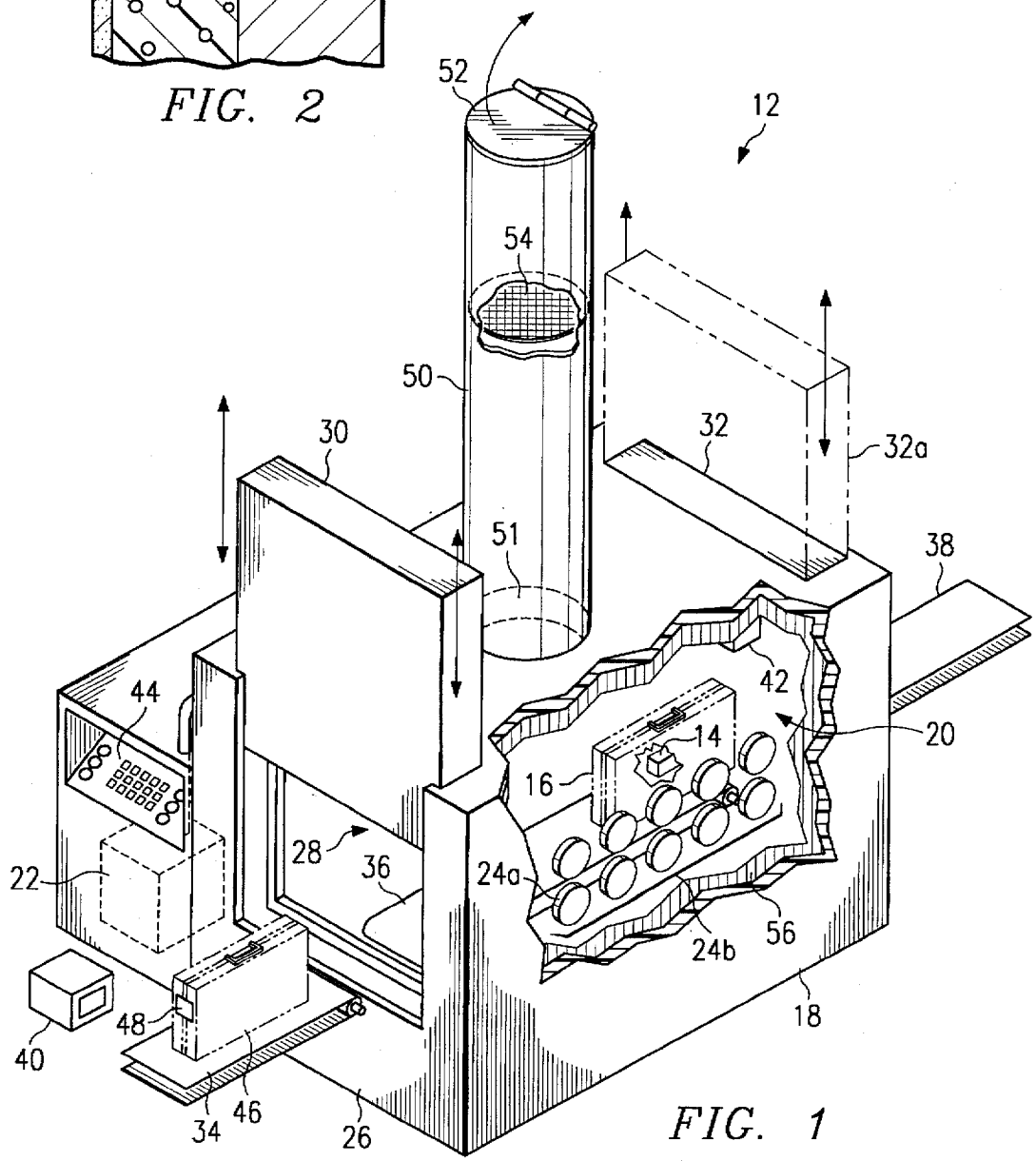
FIG. 1 is a perspective view of an apparatus according to the current invention including a partial cutaway showing the interior of the isolation enclosure containing cargo to be tested.

Referring to FIG. 1 for a better understanding of the current invention, an apparatus 12 is shown for detecting and neutralizing explosive device 14 contained in cargo 16. Apparatus 12 is comprised of an isolation enclosure 18 and a detonation inducing system. Isolation enclosure 18 has a test chamber 20 formed therewithin to contain cargo 16 to be tested. Cargo 16 may be an individual article of luggage or baggage or it may be a "batch load" comprising a plurality of such articles. Isolation enclosure 18 serves to contain and/or redirect the forces of an explosion occurring within test chamber 20 following the successful detonation of explosive device 14 until the pressures and gasses resulting from such explosion can be vented into the atmosphere. In a preferred embodiment, isolation enclosure 18 is composed of carbon steel one to three inches thick, however, those skilled in the art will appreciate that other materials such as aluminum, concrete or composites may be used. The detonation inducing system includes at least one primary energy source 22 and at least one transducer 24 compatible with said primary energy source 22. Each primary energy source 22 is adapted for the generation of a first type of energy. Such energy may include microwaves, radio frequency energy, audio frequency energy, DC electrical currents and AC electrical currents.

In a preferred embodiment of apparatus 12, each primary energy source 22 is located adjacent to, but outside, isolation enclosure 18 to minimize the possibility of damage from any explosion. One skilled in the art will appreciate, however, that many locations for primary energy source 22 are feasible provided an operative connection can be formed with transducers 24. Each compatible transducers 24 is located within the test chamber 20 of isolation enclosure 18. The compatible transducers are adapted to receive the first type of energy from at least one primary energy source 22 and to direct a second type of energy toward cargo 16 in test chamber 20. Those skilled in the art will appreciate that the exact configuration of each compatible transducer 24 will be dependent on the exact nature of the primary energy source 22 to which it is coupled. For example: where primary energy source 22 is a magnetron or a klystron or other source of microwave frequency energy, compatible transducer 24 may be a microwave antenna or wave guide; where primary energy source 22 is a radio frequency generator, compatible transducer 24 may be a directional radio frequency antenna; where primary energy source 22 is an audio frequency generator, compatible transducers 24 may be an audio frequency (acoustic) speaker; and where primary energy source 22 is a direct current or alternating current generator, compatible transducer 24 may comprise magnetic coils or electromagnets. In addition, transducer 24 may be either a single transducer (shown as 24a) or an "array" consisting of a plurality of like transducers (shown as 24b) spatially arranged within test chamber 20.

It should be noted that, for the purposes of this application, the "energy" directed by transducers 24 toward cargo 16 may include either electromagnetic energy such as microwaves and radio frequency waves as well as electrostatic and/or magnetic fields which may also be generated by certain types of transducers 24.

In operation, the energy directed by transducer 24 at cargo 16 interacts with explosive device 14 so as to detect and neutralize the explosive device through detonation. For example, electro-explosive devices such as blasting caps may be detonated by directing short bursts of low frequency, high power energy in the radio frequency spectrum at cargo 16. Similarly, electromechanical relays and mechanical switches (including pressure sensitive switches) are actuated by directing strong magnetic fields toward the cargo 16, thereby opening or closing electrical connections directly or causing deformation of ferrous metal components such as springs, diaphragms, or contacts to initiate explosive device 14. Preferably, these strong external magnetic fields are applied nearly parallel to the central axis of any coil or solenoid, and opposite to any armature or reed switch in explosive device 14. Therefore, a preferred embodiment of the current invention includes electromagnets or coils positioned on all walls of enclosure 18. In this manner, the apparatus provided by the current invention allows the detection and neutralization of explosive devices regardless of whether they emit any tell-tale vapors and or secondary radiation.

Furthermore, acoustic energy in the form of audio frequency sweeps, i.e., audio frequency energy generated by primary energy source 22 which comprises a high power audio amplifier and directed at cargo 16 by transducers 24 which comprise audio transducers (i.e., audio speakers) may be used to detonate explosive devices 14 which use pressure sensitive switches. Such switches commonly utilize a sealed chamber to which a diaphragm or bellows is connected. Therefore, when ambient pressure acts on the diaphragm or bellows, the trapped air in the chamber is compressed, causing the diaphragm to distort in a convex or concave manner or cause the bellows to expand or contract, thereby closing switch contacts and initiating an explosion. When the resonant frequency of the sealed chamber of the pressure switch is produced (typically in the range of 30–10,000 Hertz), the diaphragm or bellows of explosive device 14 will vibrate with enough force to actuate the switch numerous times, thereby simulating numerous ascent and decent cycles of the aircraft and initiating the explosive device, even if pre-programmed to require numerous cycles. In this manner, the apparatus provided by the current invention allows the detection and neutralization of pressure sensitive explosive devices regardless of whether they emit electromagnetic noise when initiated and regardless of the number of preprogrammed pressure cycles. Moreover, this neutralization is accomplished directly by forced detonation without requiring periods of waiting for an initiated device to explode of its own accord. In addition, this invention thus described provides an apparatus which simulates a large number of aircraft ascent and decent cycles in a short period of time.

Still other explosive devices 14, such as those whose primary explosive charge is detonated by a primer charge comprising a pyroignition mixture may be detected and neutralized by directing high frequency energy produced by primary energy sources 22 which comprise magnetrons or klystrons at cargo 16 in short pulses, thereby producing sufficient heat in the material to cause detonation in the same manner as the filament wire of a blasting cap. In this manner, an apparatus according to the current invention can be used for neutralizing both concealed explosive devices and batch loads of known explosive materials. The use of other, yet undiscovered means of externally detonating an explosive device is also contemplated within the scope of the current invention.

Referring again to FIG. 1, in a preferred embodiment of apparatus 12, a plurality of primary energy sources 22 producing different forms of energy will be coupled with a plurality of compatible transducers 24a or transducer arrays 24b to increase the probability of detecting and neutralizing explosive device 16. In this preferred embodiment, isolation enclosure 18 has at least one wall 26 having a passageway 28 formed therethrough and at least one door 30, 32 disposed adjacent to each passageway and movably attached to isolation enclosure 18. Each said door 30, 32 is selectively movable between an open position (shown by 30, 32a) which allows access to test chamber 20 in the interior of the isolation enclosure through passageway 28, and a closed position (shown by 32) in which said door seals the adjacent passageway. Apparatus 12 further comprises a cargo handling apparatus comprising an input means for transferring cargo 16 into said isolation enclosure 18 through at least one passageway 28, and an output means for transferring cargo out of said isolation enclosure through at least one said passage way. Referring still to FIG. 1, a cargo handling apparatus is shown in which the input means comprises belted conveyors 34 and 36 and in which the output means comprises belted conveyors 36 and 38. Those skilled in the art will appreciate that the use of belted conveyors will allow easy interface with the cargo handling systems in most airports, however, many other forms of cargo handling apparatus would be readily apparent.

When apparatus 12 detects explosive device 14 by detonation, the pressure of the resulting blast is first contained by the blast isolation enclosure 18 and any doors 30, 32 until it can be vented to atmosphere. In the preferred embodiment, isolation enclosure 18 further comprises an exhaust duct 50 connected to an exhaust duct opening 51 formed through a wall of enclosure 18. Exhaust duct 50 allows for venting any extraordinary pressures generated within isolation enclosure 18 by the etonation of explosives. Exhaust duct 50 may further comprise a flapper valve 52 and/or a shrapnel screen 54. Flapper valve 52 seals exhaust duct 50 until a predetermined pressure indicative of the detonation of an explosive is exceeded inside isolation chamber 18. Shrapnel screen 54 is positioned in the interior of exhaust duct 50 and acts to contain pieces of exploded shrapnel or debris inside isolation enclosure 18 and exhaust duct 50 while allowing venting of any extraordinary pressures.

Figure 2:
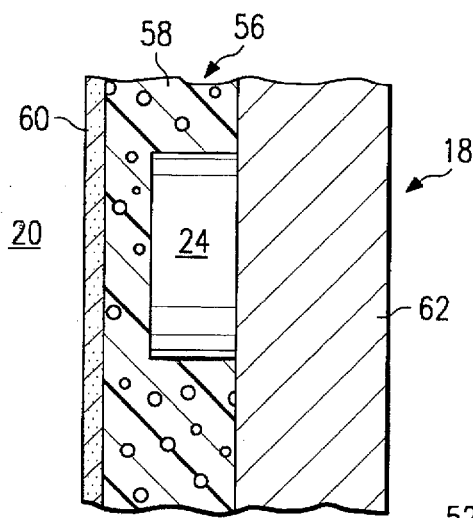
FIG. 2 is a partial sectional view of an exterior wall of the apparatus in FIG. 1 showing the blast-resistant lining.

Isolation enclosure 18 may further comprise a blast resistant lining 56. Referring now to FIG. 2, lining 56 is shown positioned in the interior of isolation enclosure 18 between test chamber 20 and enclosure wall 62. Transducer 24 is positioned between lining 56 and enclosure wall 62 so as to be protected from the effects of an explosion within test chamber 20. In the preferred embodiment, blast resistant lining 56 comprises a first layer 58 of high density closed cell glass bead impregnated plastic foam, also known as syntactic foam, and a second layer 60 of fabric comprising an organic para-aramid fiber, PPD-T, also known under the trade name "Kevlar." Those skilled in the art will appreciate that many different configurations of blast resistant lining 56 are possible, including, as shown in FIG. 2, encapsulation of transducers 24 in syntactic foam as shown and the use of Kevlar in fabric form to further protect both the syntactic foam and the transducers 24, or the use of either syntactic foam or Kevlar alone, or the use of other shielding materials.

In the preferred embodiment, apparatus 12 further comprises an automatic control system including a scanning device 40, an explosion sensor 42 and a control unit 44. Scanning device 40 is positioned to allow the scanning of cargo 46 prior to transferring said cargo into isolation enclosure 18. In the preferred embodiment, scanning device 40 is an optical bar code scanner which scans optical bar code tags 48 affixed to cargo 46. Those skilled in the art will appreciate, however, that other forms of scanning could be used, including magnetic resonance, optical character recognition and artificial intelligence means. Explosion sensor 42 is adapted to detect the occurrence of an explosion within test chamber 20 of isolation enclosure 18. In the preferred embodiment, explosion sensor 42 is a pressure detector positioned within test chamber 20 of isolation enclosure 18, however, those skilled in the art will appreciate that other types of explosion sensors could be used, including light-detectors or heat-detectors positioned within the test chamber, or acoustic- or impact-sensors positioned either inside or adjacent to isolation enclosure 18. Control unit 44 is operatively connected to the cargo handling apparatus, scanning device 40, doors 30, 32, primary energy sources 22 and explosion sensor 42. Control unit 44 would sequentially operate apparatus 12 as follows:

transfer apparatus 34, 36 moves batch load (shown in initial position as 46) into proximity with scanning device 40 which identifies article of cargo 46 by means of bar code tag 48 and allows such information to be recorded in a database if desired. Transfer apparatus 34, 36 then transfers cargo 46 into isolation enclosure 18. After isolation enclosure 18 has been sealed to the atmosphere by closing doors 30, 32 and valves 52, primary energy sources 22 are energized sending energy to transducers 24 located within isolation enclosure 18 which, in turn, direct energy or fields toward cargo (shown in test position as 16). These energies or fields interact with explosive device 14 contained within cargo 16 causing detonation. The resulting blast is first contained by isolation enclosure 18 and doors 30, 32, and then vented to the atmosphere by exhaust duct 50 and flapper valve 52. Shrapnel screen 54 traps expelled particles inside exhaust duct 50 to prevent them from being expelled into the atmosphere while the blast absorbent lining 56 protects enclosure 18 and transducers 24a or transducer array 24b. After testing, doors 30, 32 are opened and transfer apparatus 36, 38 operates to transfer cargo 16 from the enclosure.

Figure 3:
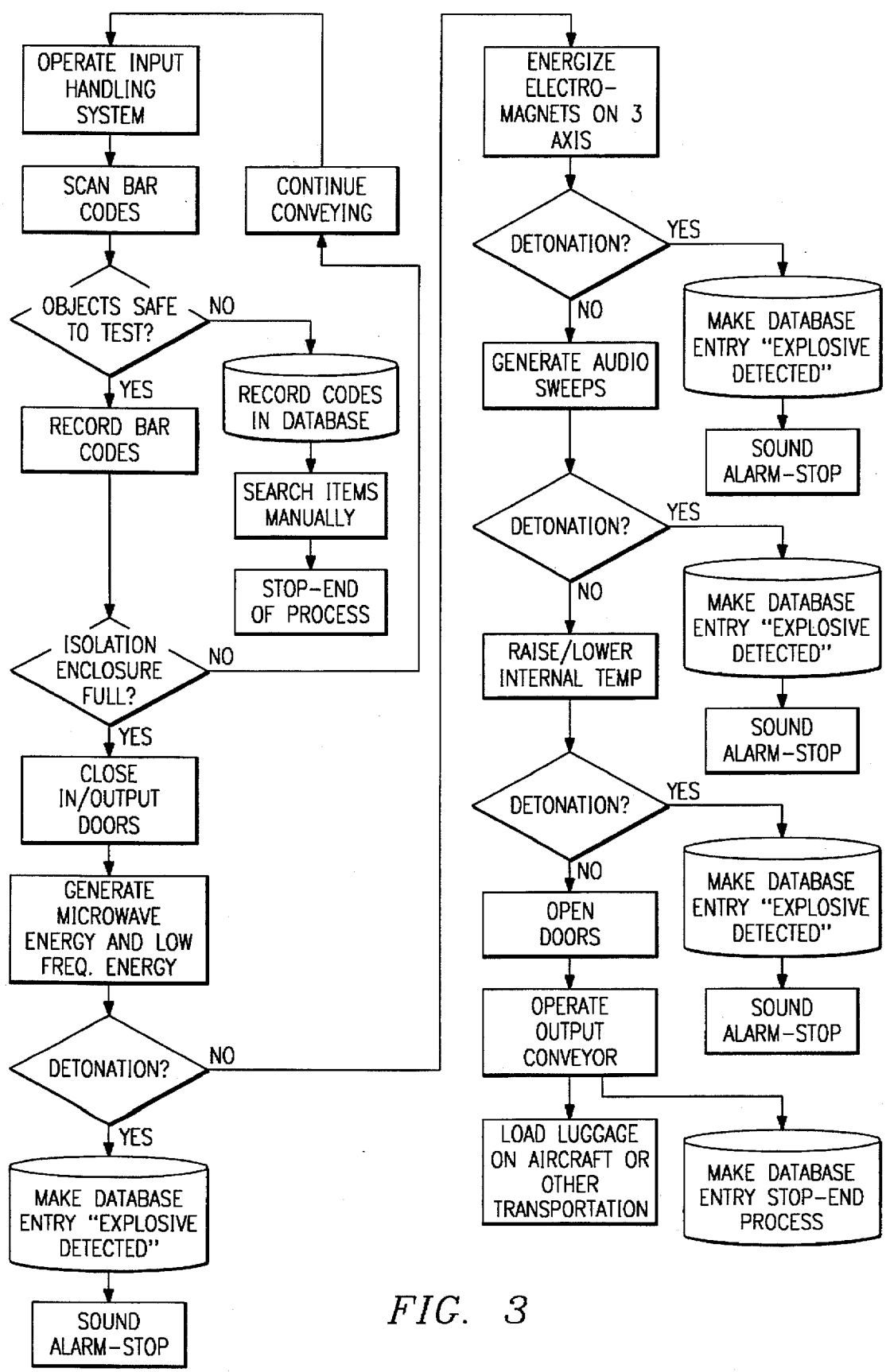
FIG. 3 is a flowchart showing a program according to the current invention to be used by the automatic control unit of the apparatus in FIGS. 1 and 2.

In the preferred embodiment, control unit 44 further comprises a microprocessor which automatically controls the sequence of operations involved in use of apparatus 12. Referring now to FIG. 3, an example of a program according to the current invention which may be used by a microprocessor to control the operation of apparatus 12 is provided.

In addition to the detection and neutralization of concealed explosive devices, this invention provides a method for the detection and neutralization of explosive devices in a batch load comprising articles of baggage or cargo. In a first embodiment, the method of the current invention comprises the steps of assembling a batch load suitable for testing in which each article of baggage or cargo has been identified; recording the identity of each article of baggage or cargo in a database; operating a transfer apparatus to position the batch load inside an isolation enclosure; sealing said isolation enclosure to form a test chamber containing the batch load; performing the following substeps for each instruction in a sequence comprising a plurality of instructions, each such instructions specifying a selected primary energy generator and selected settings therefor:

i. generating a selected type of primary energy using the selected primary energy generator and the selected settings therefor specified by the instruction;

ii. transmitting the selected primary energy from the selected generator to a compatible transducer positioned inside the enclosure;

iii. directing a secondary type of energy or field from the transducer upon receipt by the transducer of the energy from the primary generator, the secondary energy being directed at the batch load in the test chamber;

iv. detecting the presence or absence of an explosion within the test chamber using an explosion sensor; and v. continuing operation where no explosion is detected in substep iv, and where an explosion is detected in substep iv, generating an alarm signal and halting further operations;

unsealing the isolation chamber; making a database entry that the testing of articles in the batch load is completed; and operating the transfer apparatus to move the batch load out of the isolation enclosure. In a preferred embodiment of the method previously described, the step of assembling a batch load suitable for testing in which each article of baggage or cargo has been identified further comprises: operating a transfer apparatus to sequentially position each article of baggage or cargo in operative relationship with a scanning device; scanning each article with the scanning device until an identity for the article is determined; comparing the identity of each article against a set of criteria for testing suitability; accepting the article if its identity matches the set of criteria for testing suitability, and rejecting the article if its identity does not match the set of criteria for testing suitability; operating the transfer apparatus to selectively route articles which were accepted to a first location and selectively route articles which were rejected to a second location; accumulating articles which were accepted in the first location until a preselected number of articles representing a batch load is present.

Although the apparatus and method of the present invention have been described with respect to specific embodiments thereof, various changes and modifications to the preferred embodiments may be suggested to those skilled in the art, and it is intended that the present invention encompass such changes and modifications as fall within the scope of the appended claims.

I claim:

1. An apparatus for detecting and neutralizing an explosive device having a detonator including a pressure sensitive switch, said explosive device being concealed in cargo as a bomb, said apparatus comprising:

an isolation enclosure including a wall, a door, and an exhaust duct opening formed through said wall;
said wall defining a test chamber set apart from an external environment having an ambient pressure;
said door being movably attached to said wall and being selectively movable between an open position and a closed position wherein, when in said open position, said door uncovers a loading passageway formed in said wall between said test chamber and said external environment and, when in said closed position, said door blocks said loading passageway;
said exhaust duct opening connecting said test chamber to an exhaust duct routed in a pre-selected direction; and a detonation-inducing system including a signal generator and an audio transducer;
said signal generator producing at an output an audio sweep signal having a frequency ranging across a frequency interval within the range from about 5 to 15,000 Hertz;
said output of said signal generator being operably connected to said audio transducer;
said audio transducer being positioned within said test chamber and emitting an acoustic signal into said test chamber;
said acoustic signal having a frequency equal to said frequency of said audio sweep signal and, when said explosive device is within said test chamber with said door in said closed position, inducing a mechanical vibration of said pressure sensitive switch causing said switch to activate repeatedly thereby activating said detonator of said explosive device;

whereby said explosive device is neutralized and any shrapnel produced therefrom is blocked from passing through said loading passageway by said door but can pass through said exhaust duct opening into said exhaust duct.

2. An apparatus according to claim 1, wherein said audio sweep signal has a frequency ranging across a frequency interval within the range of about 30 to 10,000 Hertz.

3. An apparatus according to claim 1, wherein said exhaust duct is connected to said external environment for maintaining said test chamber at said ambient pressure.

4. An apparatus according to claim 1, further comprising a cargo handing apparatus including:

(a) an input means for transferring cargo into said isolation enclosure through said passageway; and
(b) an output means for transferring cargo out of said isolation enclosure.

5. An apparatus according to claim 4, further comprising an automatic control system including:

(a) a scanning device being positioned to allow scanning said cargo prior to transferring said cargo into said isolation enclosure;
(b) an explosion sensor for detecting the occurrence of an explosion within said isolation enclosure; and
(c) a control unit being operatively connected to said cargo handling apparatus, said scanning device, said door, said detonation-inducing system, and said explosion sensor.

6. An apparatus according to claim 5, wherein said control unit further comprises a microprocessor.

7. An apparatus according to claim 5, wherein said scanning device comprises an optical bar code scanner.

8. An apparatus according to claim 1, wherein said isolation enclosure further comprises a blast-resistant lining being positioned in said test chamber adjacent to said wall.

9. An apparatus according to claim 8, wherein said blast-resistant lining comprises high density closed cell glass bead impregnated plastic foam.

10. An apparatus according to claim 8, wherein said blast-resistant lining comprises fabric comprising an organic para-aramid fiber.

11. An apparatus according to claim 1, further comprising a radio frequency signal generator and an antenna;

said radio frequency signal generator producing at an output a radio frequency signal;

said output of said radio frequency signal generator being operably connected to said antenna;

said antenna directing radio frequency energy into said test chamber;

said radio frequency energy, when said explosive device is within said test chamber with said door in said closed position and said explosive device has not been neutralized by said acoustic signal, inducing an electrical current in a conductive portion of said detonator of said explosive device and causing said detonator to activate;

whereby said explosive device is neutralized.

12. An apparatus according to claim 11, wherein said radio frequency generator comprises a magnetron.

13. An apparatus according to claim 11, wherein said radio frequency generator comprises a klystron.

14. An apparatus for neutralizing an explosive device having a detonator operating switch including a ferromagnetic component, said explosive device being concealed by a criminal in cargo as a bomb, said apparatus comprising:

an isolation enclosure including a wall and a door, and an exhaust duct opening formed through said wall;

said wall defining a test chamber set apart from an external environment;

said door being movably attached to said wall and being selectively movable between an open position and a closed position wherein, when in said open position, said door uncovers a loading passageway formed in said wall between said test chamber and said external environment and, when in said closed position, said door blocks said loading passageway;

said exhaust duct opening connecting said test chamber to an exhaust duct routed in a pre-selected direction; and a magnetic field producer comprising a direct current generator connected to a magnetic transducer, said magnetic transducer being positioned on said wall and producing a magnetic field in said test chamber, said magnetic transducer being selected from the group consisting of at least one direct current magnetic coil and at least one direct current electromagnet;

said magnetic field, when said explosive device is within said test chamber and said door in said closed position, exerting a sustained mechanical force on said ferromagnetic component;

whereby said component is deformed or moved into contact with another component of the detonator operating switch in a manner unintended by said criminal thereby neutralizing said explosive device.

15. An apparatus according to claim 14, further comprising:

said isolation enclosure having four walls; and said magnetic field producer comprising four direct current electromagnets, one of said magnets being positioned on each of said four walls of said isolation enclosure.

16. A method for detecting and neutralizing an explosive device having a pressure sensitive switch, said explosive device being concealed in cargo as a bomb, said method comprising the steps of:

(i) placing said cargo and said explosive device having said pressure sensitive switch within a test chamber defined by a wall of an isolation enclosure;

said test chamber having a test chamber pressure and being set apart from an external environment having an ambient pressure;

(ii) producing an acoustic signal in said test chamber by at least one audio transducer within said test chamber;

said acoustic signal having a frequency ranging across a frequency interval within the range of about 5 to 15,000 Hertz;

(iii) inducing with said acoustic signal a mechanical vibration of said pressure sensitive switch causing said switch to activate repeatedly and to detonate said explosive device.

17. A method according to claim 16, wherein said isolation enclosure maintains said test chamber pressure equal to said ambient pressure.

* * * * *